United States Patent
Steiger et al.

(10) Patent No.: US 7,485,135 B2
(45) Date of Patent: Feb. 3, 2009

(54) DEVICE FOR FIXING SURGICAL IMPLANTS

(75) Inventors: Peter Steiger, Herzogenbuchsee (CH); Robert Frigg, Bettlach (CH); Lukas Eschbach, Bettlach (CH)

(73) Assignee: Synthes (U.S.A.), West Chester, PA (US)

( * ) Notice: Subject to any disclaimer, the term of this patent is extended or adjusted under 35 U.S.C. 154(b) by 533 days.

(21) Appl. No.: 10/382,868

(22) Filed: Mar. 7, 2003

(65) Prior Publication Data
US 2003/0199877 A1    Oct. 23, 2003

(51) Int. Cl.
*A61B 17/84* (2006.01)
(52) U.S. Cl. ............................................. 606/300
(58) Field of Classification Search ............ 606/72, 606/75, 76, 151, 155, 232; 411/38, 42–43
See application file for complete search history.

(56) References Cited

U.S. PATENT DOCUMENTS

| | | | |
|---|---|---|---|
| 3,065,661 A | 11/1962 | Kolec et al. | |
| 4,620,825 A * | 11/1986 | Potzas | ............ 411/34 |
| 4,810,141 A | 3/1989 | Rainville | |
| 4,897,003 A * | 1/1990 | Bradley et al. | ............ 411/43 |
| 5,713,903 A * | 2/1998 | Sander et al. | ............ 606/72 |
| 5,919,194 A * | 7/1999 | Anderson | ............ 606/72 |
| 6,299,398 B1 * | 10/2001 | Shinjo | ............ 411/43 |
| 6,406,234 B2 * | 6/2002 | Frigg | ............ 411/42 |

FOREIGN PATENT DOCUMENTS

| | | |
|---|---|---|
| EP | 0998878 | 5/2000 |
| FR | 2141020 | 1/1973 |
| FR | 2552830 | 4/1985 |
| GB | 2054082 | 2/1981 |
| WO | WO 99/62417 | 12/1999 |

* cited by examiner

*Primary Examiner*—Eduardo C Robert
*Assistant Examiner*—Richard Shaffer
(74) *Attorney, Agent, or Firm*—Fay Kaplun & Marcin, LLP

(57) ABSTRACT

A device for treating bone fractures and/or for fixing surgical implants, surgical threads or tissues in or on the bone comprising a closing element and a rivet. The rivet includes a shaft extending from a rear end to a front end coaxial to a central axis and having a through-hole extending coaxially therethrough. The shaft of the closing element is coaxially displaceable in the through-hole and the head of the closing element can be axially brought to rest on the front shaft end. The rivet also comprises at least two grooves on the outside, these grooves extending from the front shaft in the direction of the rear end, parallel to the central axis.

20 Claims, 4 Drawing Sheets

Section I-I

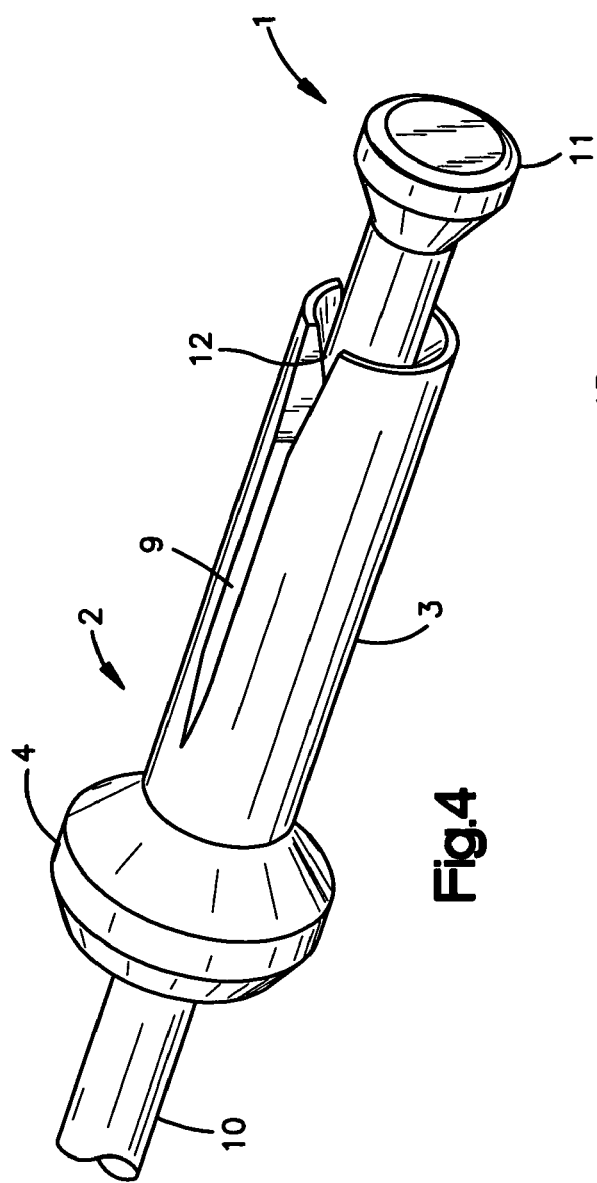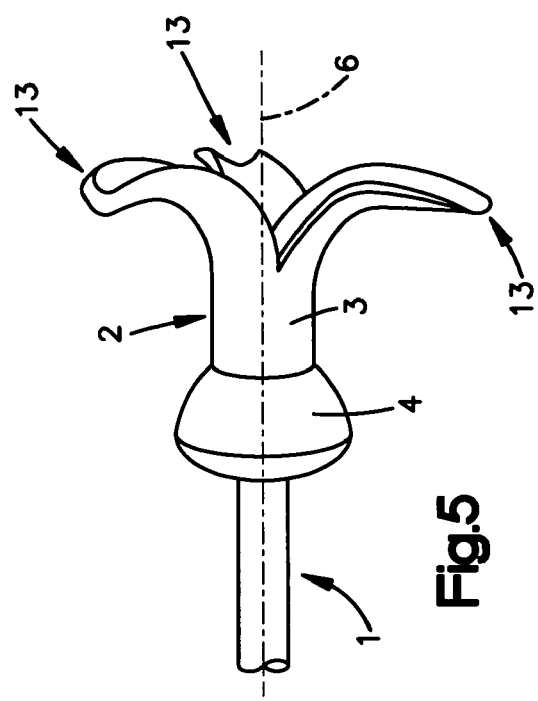

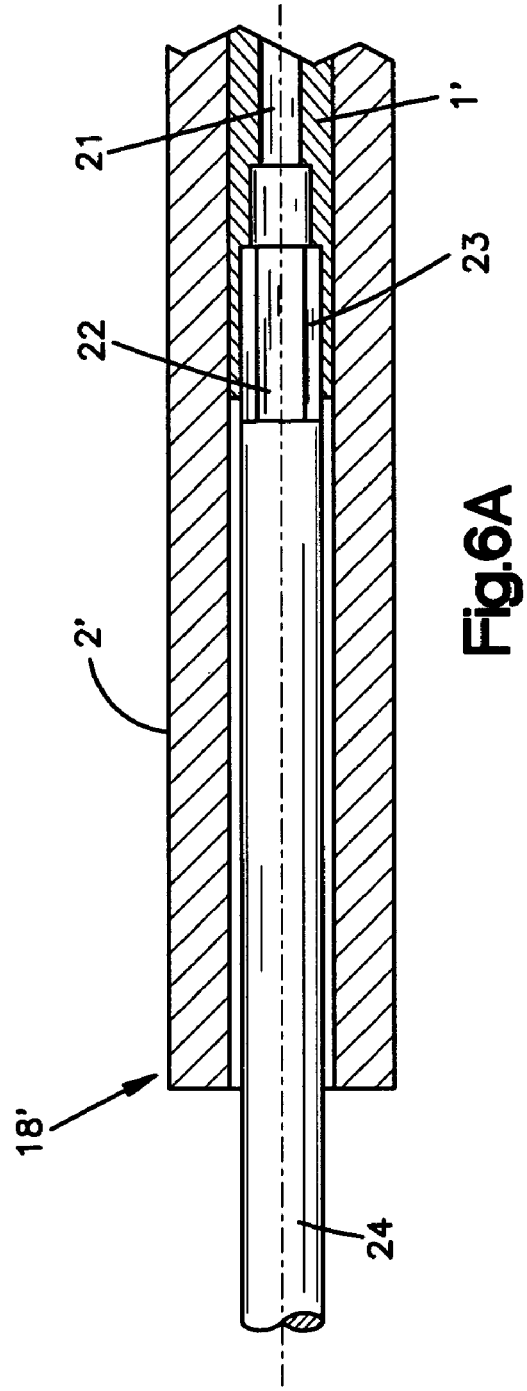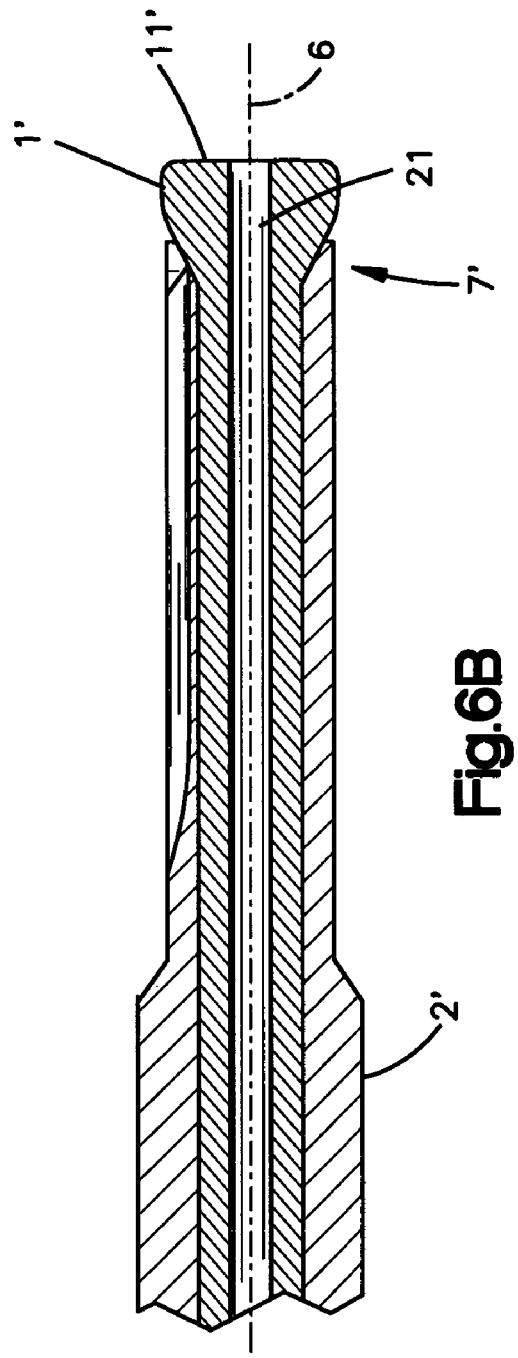

DEVICE FOR FIXING SURGICAL IMPLANTS

FIELD OF THE INVENTION

The invention relates to a device for the treatment of fractures of bones and/or for fixing surgical implants, surgical threads, or tissues in or on the bone.

BACKGROUND OF THE INVENTION

For the surgical treatment of fractures of bones or for fixing surgical implants, threads, or tissues in or on the bone, even rivets, in particular blind rivets, can be used. Particularly suitable are rivets with closing heads formed of separate anchoring tongues spread relatively wide. Such blind rivets are disclosed in the non-medical area, e.g. in UK Patent Application No. GB 2,054,082 to Tucker Fasteners. The anchoring tongues are formed by axial tearing of the wall of the rivet shaft at the front end of the blind rivet by means of a pyramid-shaped, sharp-edged closing head which is drawn into the hollow cylindrical rivet shaft from the front end. At least one disadvantage of these types of blind rivets is their limited application to soft materials and the necessity of high closing forces for forming the closing head on the blind rivet.

A need exists for an improved medically applicable fixation means, in particular a surgically applicable blind rivet which provides materials with high strength, e.g. titanium, and can be fixed by means of closing forces acceptable in surgery. A need also exists that the device be suitable for the treatment of fractures of bones and/or for fixing surgical implants, surgical threads, or tissues in or on the bone.

SUMMARY OF THE INVENTION

The present invention generally relates to a device comprising a closing element with a shaft and at the end position a head which is fixedly connected to the shaft or, for example, can be connected by means of a thread connection, to the shaft, and a rivet which comprises, coaxial to a central axis, a rivet shaft and a through-hole coaxially penetrating the rivet.

The shaft of the closing element can be displaced coaxially in the through-hole so that the head can be brought axially to lie at the front shaft end. The head and shaft of the closing element can be structured in two parts or as one part. Furthermore, the rivet shaft includes two grooves which extend from the front shaft end parallel to the central axis over a length L in the direction of the rear end of the rivet. The grooves serve as theoretical break points so that on further displacement of the closing element in the direction of the rivet head the rivet shaft is divided by the head of the closing element into anchoring tongues on a part of its overall length. In one preferred embodiment, the ratio of the length L to the overall length of the rivet shaft is between 20% and 90%.

In another preferred embodiment of the device according to the invention, the rivet shaft includes at least one slot, each slot having a first end intersecting the front shaft end and extending into the through-hole and a second end extending parallel to the central axis into a groove. In another embodiment, the rivet includes at its rear end a rivet head which can be fixedly connected to the rivet or, for example, can be connected to the shaft by means of a thread connection.

In another embodiment of the device according to the invention, the characteristic values of the rivet material lie within a range of the ratio of tensile strength to elongation at break of 10:1 to 50:1, preferably 10:1 to 30:1.

In still another embodiment of the device according to the invention, the geometric dimensions of the rivets are chosen so that the ratio of the outer diameter da of the rivet shaft to the diameter d of the through-hole lies in a range from 1.1:1 to 2.5:1, preferably from 1.5:1 to 2:1. The ratio of the radial depth t of the grooves to the wall thickness of the rivet shaft lies suitably in a range from 1:1.2 to 1:2.5, preferably from 1:1.7 to 1:2.3. The wall thickness can be determined from the difference of the outer diameter da and the diameter d.

BRIEF DESCRIPTION OF THE DRAWINGS

Preferred features of the present invention are disclosed in the accompanying drawings, wherein similar reference characters denote similar elements throughout the several views, and wherein:

FIG. 4 is a perspective view of the device of FIGS. 1 to 3.

FIG. 5 is a perspective view of the device of FIGS. 1-4 in the closed state.

FIGS. 6A and 6B are left and right side longitudinal cross-sectional views, respectively, of another embodiment of the device according to the invention.

DETAILED DESCRIPTION OF THE PREFERRED EMBODIMENTS

Figure 1:
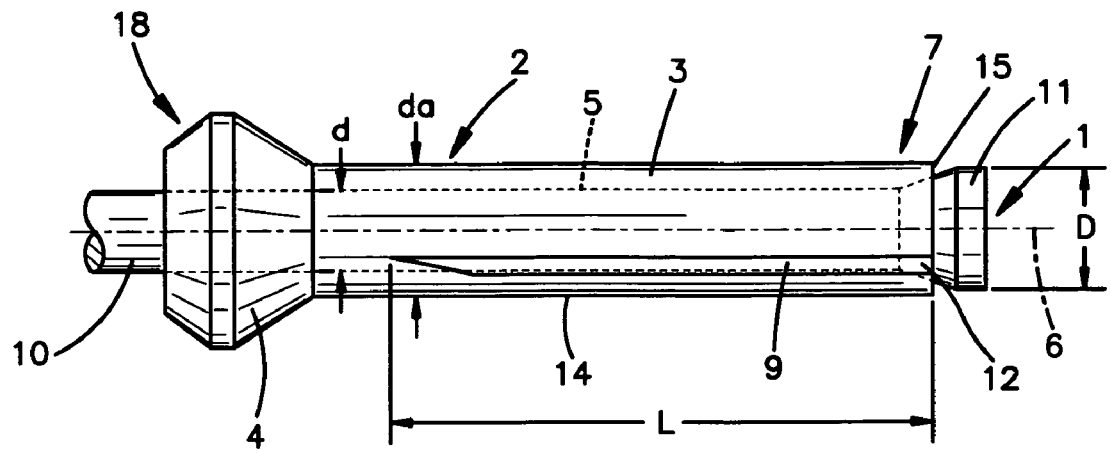
FIG. 1 is a top view of the device according to the invention.

Referring to FIG. 1, a rivet 2 and a closing element 1 according to one embodiment of the device according to the invention are represented. The rivet 2 has a central axis 6 and comprises a cylindrical rivet shaft 3 running parallel to the central axis 6. In a preferred embodiment, the cylindrical rivet shaft is not necessarily required to be circularly cylindrical. A rivet head 4 is fixedly connected to the rivet shaft 3, and a cylindrical through-hole 5 penetrates the rivet 2 coaxially along the central axis 6. The rivet shaft 3 has an outer diameter da and includes grooves 9 which run parallel to the central axis 6, and extend from the front shaft end 7 over a length L, and have a depth t from the outer circumferential surface 14. The depth t is determined so that the wall thickness, defined by the diameter da and d and the depth t, on closing of the rivet 2 with the closing element 1 allows a separation of the rivet 2 into separate anchoring tongues 13 (FIG. 5) on the part to be closed. In a preferred embodiment, the number of anchoring tongues 13 corresponds to the number of grooves 9 introduced on the outer circumferential surface 14 of the rivet 2.

The grooves serve as theoretical break points so that on further displacement of the closing element in the direction of the rivet head the rivet shaft is divided by the head of the closing element into anchoring tongues on a part of its overall length. In this embodiment, the ratio of the length L to the overall length of the rivet shaft may be between 20% and 90% so that the anchoring tongues can expand radially to a surface F which can be 3 to 20 times the cross-sectional surface of the rivet shaft. The number of the grooves distributed uniformly on the circumference of the rivet shaft may be in a range of 3 to 8, preferably 3 to 5. From the number of grooves the number of anchoring tongues in the fixed rivet also follows. In the embodiment of the rivet 2 represented here, the wall thickness of the rivet shaft 3 corresponds to 14% of the outer diameter da. From the front apical face 15 of the rivet shaft 3, slots 12 penetrate into the rivet shaft 3 parallel to the central axis 6. The slots run, on one side, at the front shaft end 7 into the through-hole 5 and, on the other side, parallel to the central axis 6 into the grooves 9.

The closing element 1 comprises a shaft 10 parallel to the central axis 6 and at the end position a head 11 is disposed which runs in the form of a wedge into the shaft 10. The closing of the rivet 2 is accomplished after the introduction of the rivet 2, e.g. into a bone plate and a bone (not represented) by means of the closing element 1. The head 11 of the closing element 1 has a diameter D which is greater than the diameter d of the through-hole 5 so that the head 11 of the closing element 1 is pressed into the inner cone 8 (FIG. 2) of the through-hole 5 by means of a tractive force exerted on the shaft 10. On pressing the widening wedge-like head 11 of the closing element 1 into the inner cone 8 (FIG. 2) in the through-hole 5, the wall 20 (FIG. 2) of the rivet shaft 3 is expanded and on further pressing of the head 11 of the closing element 1 separated into the anchoring tongues 13 (FIG. 5) at the theoretical break points formed by the grooves 9.

Figure 2:
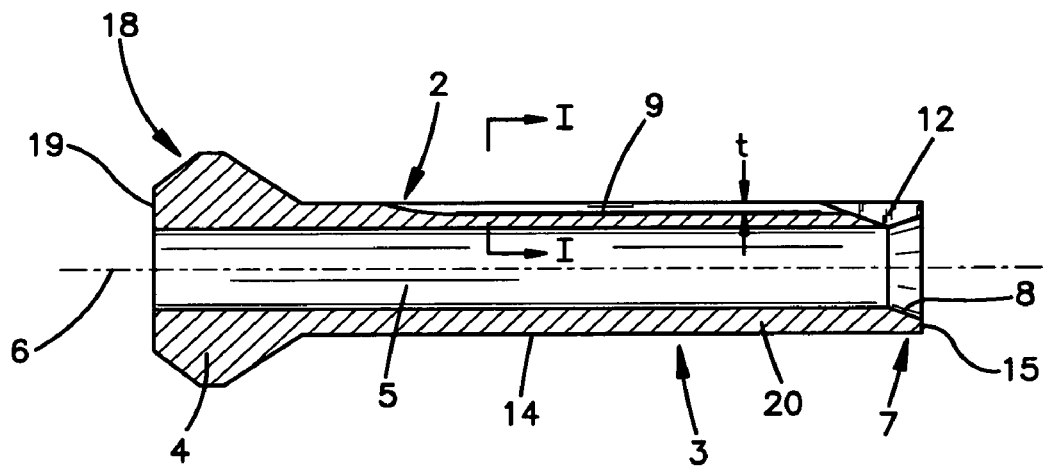
FIG. 2 is a longitudinal cross-sectional view through the embodiment of the device according to the invention represented in FIG. 1.
Figure 3:
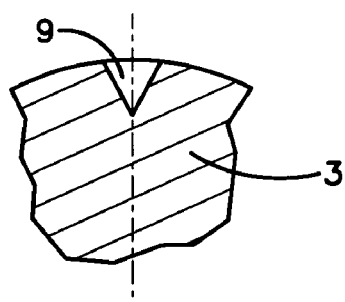
FIG. 3 is a cross-sectional view taken along line I-I of FIG. 2.

Referring to FIG. 2, a cross-section of the rivet is represented which corresponds to the above-described embodiment of the device according to the invention. The rivet 2 comprises a central axis 6, a circularly cylindrical rivet shaft 3 with a front shaft end 7 intersecting the central axis 6, and at its rear end 18 intersecting the central axis 6 at the end position a rivet head 4, also circularly cylindrical. At the front shaft end 7 there is a front apical face 15 perpendicular to the central axis 6. The rivet head 4 runs against the front shaft end 7 directed convexly or tapering in the form of a wedge into the rivet shaft 3 and also convexly or tapering in the form of a wedge into the rear apical face 19 of the rivet 2. The rear apical face lies at the end position at its rear end 18. A through-hole 5 penetrates coaxially to the central axis 6 and the rivet 2 from the front shaft end 7 up to the rear end 18. The through-hole 5 runs at the front shaft end 7 with the inner cone 8 expanding into the front apical face 15. Parallel to the central axis 6, grooves 9 are introduced which penetrate from the front shaft end 7 up to a length L (FIG. 1) into the rivet shaft 3 and have a V-shaped cross-section (FIG. 3) perpendicular to the central axis 6. Moreover, slots 12 penetrate into the rivet shaft 3 from the front apical face 15 also parallel to the central axis 6. These slots 12 have a rectangular cross-section (FIG. 1) perpendicular to the central axis 6 and have a wedge-like structure parallel to the central axis 6. The slots 12 run parallel to the central axis 6 and run into the front apical face 15, into the outer circumferential surface 14, and into the grooves 9. The tearing of the rivet shaft is promoted by these slots. At least one of the slots extends from a first end intersecting with the corresponding groove and extending toward the front end of the shaft tapering through a thickness of the shaft toward the central axis to open into the through-hole.

FIG. 5 shows the rivet 2 with central axis 6, rivet head 4, expanded rivet shaft 3, and closing element 1 in the closed state of the rivet 2. The rivet shaft 3 is expanded to the length L (FIG. 1) and comprises three anchoring tongues 13.

In one preferred embodiment, the rivet may have the following geometric dimensions: the outer diameter da of the rivet shaft may be 2 to 12 mm, preferably 3 to 8 mm; diameter d of the through-hole may be 1 to 8 mm, preferably 1.5 to 5 mm; wall thickness of the rivet shaft may be 0.2 to 4 mm, preferably 0.5 to 2 mm; and radial depth t of the grooves may be 0.1 to 3 mm, preferably 0.2 to 1 mm. In another embodiment of the device, the geometric dimensions of the rivets are selected so that the ratio of the outer diameter da of the rivet shaft to the diameter d of the through-hole is in a range from 1.1:1 to 2.5:1, preferably from 1.5:1 to 2:1.

The ratio of the radial depth t of the grooves to the wall thickness of the rivet shaft may be in a range from 1:1.2 to 1:2.5, preferably from 1:1.7 to 1:2.3. The wall thickness can be determined from the difference of the outer diameter da and the diameter d. In an additional embodiment, the grooves may have a triangular cross-section perpendicular to the central axis where the apical angle of the triangle in the base of the groove lies within a range of 30° to 80°, preferably of 40° to 70°.

The rivet material is preferably metallic and may include the following materials or alloys: a) materials based on iron, preferably steel, b) materials based on titanium, preferably Ti CP and titanium alloys, c) materials based on cobalt, preferably cobalt alloys, d) materials based on tantalum, preferably tantalum alloys, and e) materials based on zirconium, preferably zirconium alloys. In another embodiment, the rivet may be made from a material having the following physical properties or characteristics: the ratio of tensile strength (Rm in N/mm2) to elongation at break (A5 in %) is between 10:1 to 50:1, preferably between 10:1 to 30:1.

Figure 7:
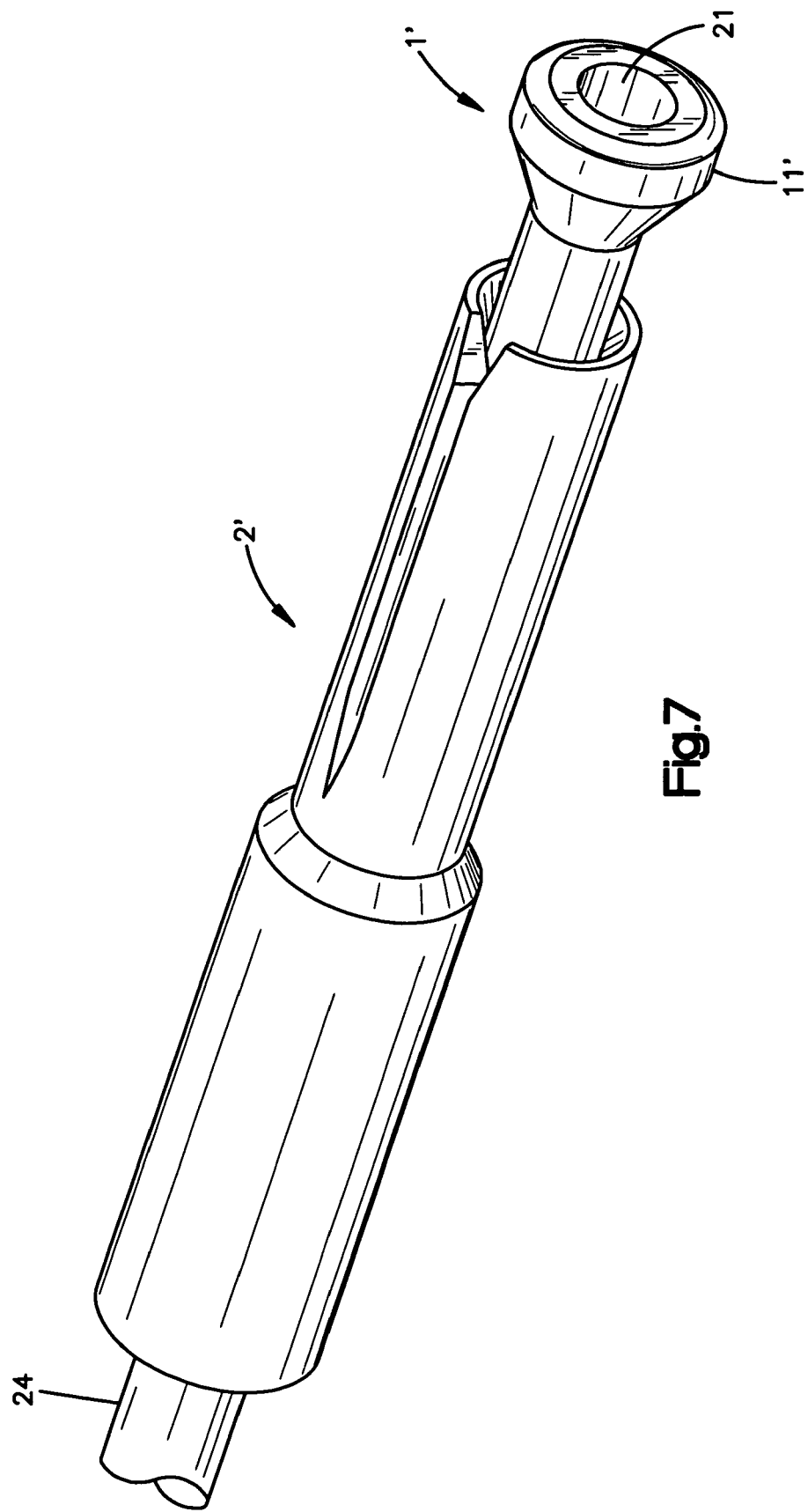
FIG. 7 is a perspective view of the device of FIGS. 6A and 6B.

Referring to FIGS. 6A, 6B, and 7, another embodiment of the rivet 2 is represented which is distinguished from the forms of embodiment represented in FIGS. 1 and 2 in that the rivet 2' includes no rivet head 4 (FIGS. 1 and 2) at its rear end 18'. Furthermore, the closing element 1' penetrates the rivet 2' only on a part of its overall length and is structured with a hole 21 penetrating the closing element 1' coaxially. The hole is provided at its end 22 lying axially opposite the head 11' with a coaxial inner thread 23. A Kirschner wire 24 can be screwed into this inner thread and can be screwed out of the inner thread 23 once again after the closing of the rivet 2'.

It will be appreciated that a more homogeneous introduction of force into the bones is possible as compared to the use of screws, and generally a more stable anchoring can be produced compared to bone screws, even with poor bone quality.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. A device for fixing surgical implants comprising a rivet, the rivet comprising:

a rivet shaft extending from a rear end to a front end coaxial to a central axis and having an outer circumferential surface, the front end positioned axially opposite the rear end, the rivet having a cylindrical through-hole extending coaxially there through, and at least two grooves extending along the outer circumference between the front end and the rear end and parallel to the central axis over a length L, the grooves having a radial depth t measured from the outer circumferential surface, the radial depth t less than the radial depth from the outer circumferential surface to the through-hole prior to a tearing of the rivet shaft into a closed state, wherein:

the rivet is formed from a material having a ratio of tensile strength (Rm in N/mm2) to elongation at break (A5 in %) of between 10:1 and 50:1; and the rivet shaft defines at least one slot having a first end intersecting the shaft front end and extending into the through-hole and a second end extending parallel to the central axis into a corresponding one of the grooves prior to a tearing of the rivet shaft into a closed state, the at least one slot extending from a first end intersecting with the corresponding groove and extending toward the front end of the shaft tapering through a thickness of the shaft toward the central axis to open into the through-hole.

2. The device of claim 1, wherein the rivet shaft has an overall length defined by the distance from front end to the rear end, the rivet shaft having a ratio of the length L to the overall length of the rivet shaft of between 20% and 90%.

3. The device of claim 1, wherein the ratio of the outer diameter of the rivet shaft to the diameter of the through-hole is in a range from 1.1:1 to 2.5:1.

4. The device of claim 1, wherein the ratio of the radial depth of the grooves to the wall thickness of the rivet shaft is in a range from 1:1.2 to 1:2.5.

5. The device of claim 1, further comprising a closing element having a shaft and a head positioned at one end thereof, and the shaft of the closing element can be displaced coaxially in the through-hole and the head can be brought axially toward the front shaft end.

6. The device of claim 1, wherein the rivet includes an enlarged head at its rear end.

7. A device for fixing surgical implants comprising:

a rivet comprising a shaft extending longitudinally from a front end to a rear end and having an outer circumferential surface, the shaft defining a central axis from the front end to the rear end and having a cylindrical through-hole extending coaxially there through from the front end to the rear end, the through-hole having a diameter, the shaft also having a groove extending longitudinally along a portion of the outer circumferential surface between the front end and the rear end, the groove extending partially into the shaft from the outer circumferential surface towards the through-hole to a depth less than that of the through-hole prior to a tearing of the rivet shaft into a closed state, the shaft further having a slot extending longitudinally from the front end into the groove, the slot penetrating completely through from the outer circumferential surface to the through-hole at the front end and tapering away from the central axis through the thickness of the shaft to intersect with the groove prior to a tearing of the rivet shaft into a closed state; and a closing element comprising:

a shaft extending longitudinally from a front end to a rear end, the shaft of the closing element inserted through the through-hole of the rivet shaft, the front and rear ends of the closing element shaft each extending beyond the respective front and rear ends of the rivet shaft, and an enlarged head extending from the front end of the closing element shaft and adjacent the front end of the rivet shaft, the enlarged head having a diameter larger than the diameter of the rivet shaft through-hole.

8. The device of claim 7 wherein the closing element has a through-hole extending longitudinally from the front end to the rear end of the closing element shaft and through the enlarged head of the closing element.

9. The device of claim 8 wherein the through-hole of the closing element has an inner thread.

10. The device of claim 9 further comprising a Kirschner wire operative to be threaded into and out of the inner thread of the closing element through-hole.

11. The device of claim 7 wherein the enlarged head of the closing element is wedge shaped.

12. The device of claim 7 wherein the enlarged head of the closing element is integrally connected to the shaft of the closing element.

13. The device of claim 7 wherein the slot has a rectangular cross section perpendicular to the central axis prior to a tearing of the rivet shaft into a closed state.

14. The device of claim 7 wherein the groove has a V-shaped cross section perpendicular to the central axis prior to a tearing of the rivet shaft into a closed state.

15. The device of claim 7 wherein the front end of the rivet shaft has an inner cone shape extending from the outer circumferential surface to the through-hole prior to a tearing of the rivet shaft into a closed state.

16. The device of claim 7 wherein the rivet shaft is cylindrical prior to a tearing of the rivet shaft into a closed state.

17. The device of claim 7 further comprising:

three to eight of the grooves and slots of the rivet shaft prior to a tearing of the rivet shaft into a closed state, the three to eight grooves and slots distributed uniformly around the outer circumferential surface of the shaft; and three to eight anchoring tongues after tearing of the rivet shaft into a closed state.

18. The device of claim 7 wherein the rivet further comprises an enlarged head extending from the rear end of the shaft and having a through-hole aligned with the through-hole of the shaft.

19. The device of claim 18 wherein the enlarged head of the rivet has a first convex or tapering wedge shape facing the rivet shaft and a second convex or tapering wedge shape facing away from the rivet shaft.

20. The device of claim 18 wherein the enlarged head of the rivet is threadedly connected to the rivet shaft.

* * * * *